(12) United States Patent
Wu et al.

(10) Patent No.: US 8,093,280 B2
(45) Date of Patent: Jan. 10, 2012

(54) METHODS OF PREPARING IMIDAZOLE-BASED COMPOUNDS

(75) Inventors: Wenxue Wu, Princeton, NJ (US); Jie Yan, Plainsboro, NJ (US); Haiming Zhang, Lawenceville, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 12/885,738

(22) Filed: Sep. 20, 2010

(65) Prior Publication Data

US 2011/0071303 A1    Mar. 24, 2011

Related U.S. Application Data

(63) Continuation of application No. 12/101,410, filed on Apr. 11, 2008, now Pat. No. 7,812,174.

(60) Provisional application No. 60/923,029, filed on Apr. 12, 2007.

(51) Int. Cl.
*A61K 31/417* (2006.01)
*C07D 233/64* (2006.01)

(52) U.S. Cl. .................... 514/396; 548/300.1

(58) Field of Classification Search ............... 548/300.1; 514/396

See application file for complete search history.

(56) References Cited

U.S. PATENT DOCUMENTS

| 4,567,194 | A | 1/1986 | Kroeplien |
| 7,649,098 | B2* | 1/2010 | Augeri et al. ............. 548/336.1 |
| 7,812,174 | B2 | 10/2010 | Wu |
| 2008/0275099 | A1 | 11/2008 | Wu |

OTHER PUBLICATIONS

Cliff and Pyne, *J. Org. Chem.*, 62: 1023-1032 (1997).
Cliff and Pyne, *Tett. Letters*, 36(33): 5969-5972 (1995).
Halweg and Buchi, *J. Org. Chem.*, 50(7): 1134-6 (1985).
Search Report and Written Opinion for Corresponding International Application PCT/US2008/060032, dated Oct. 13, 2009.

* cited by examiner

*Primary Examiner* — Kamal Saeed
*Assistant Examiner* — Janet L Coppins
(74) *Attorney, Agent, or Firm* — Max Bachrach

(57) ABSTRACT

Methods of preparing imidazole-based compounds are disclosed. Particular compounds are of formula I.

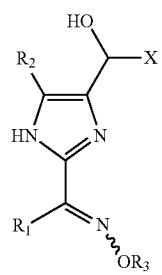

8 Claims, 1 Drawing Sheet

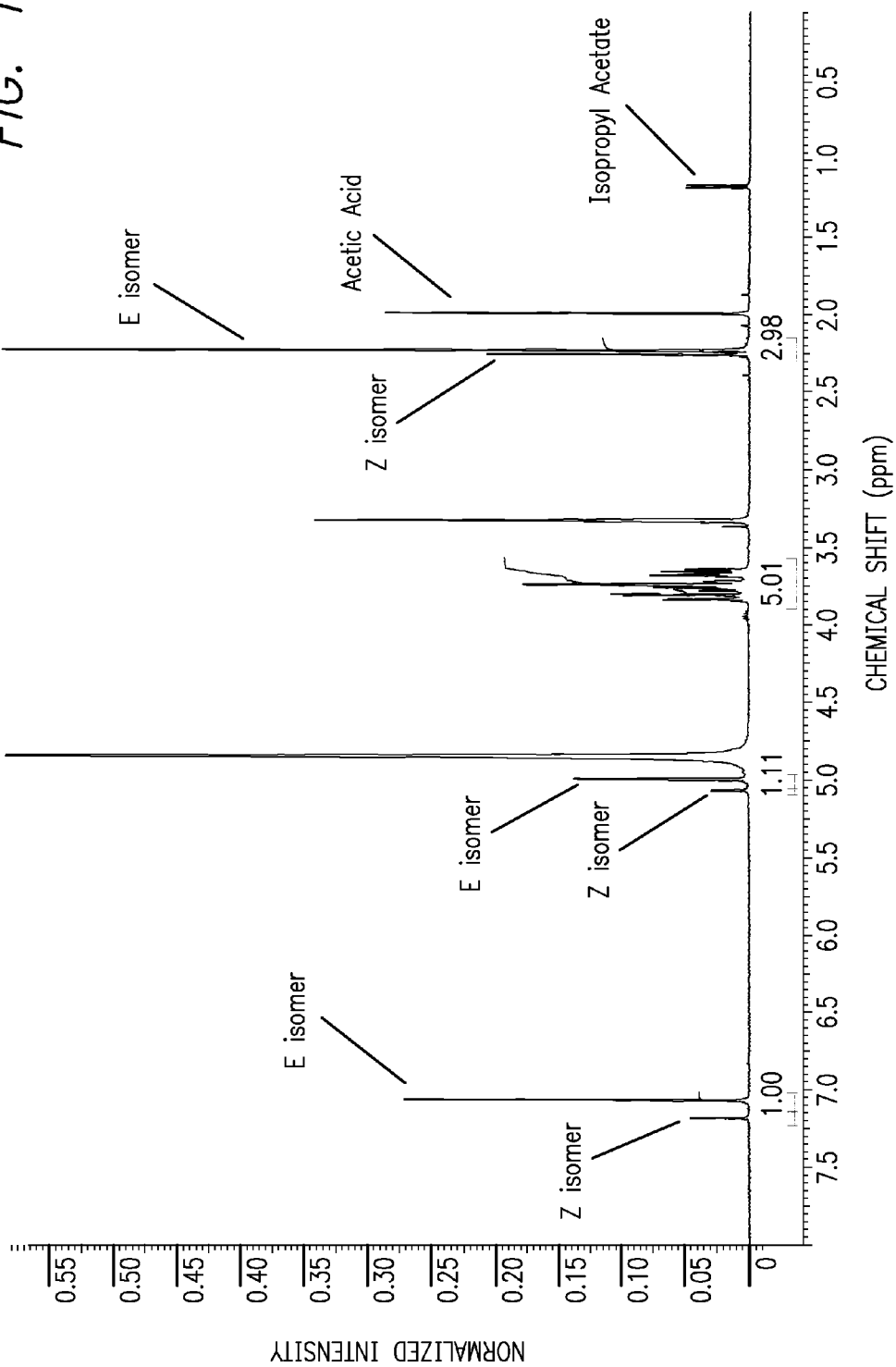

US 8,093,280 B2

METHODS OF PREPARING IMIDAZOLE-BASED COMPOUNDS

This application is a continuation of U.S. patent application Ser. No. 12/101,410, filed Apr. 11, 2008, which claims priority to U.S. provisional application No. 60/923,029, filed Apr. 12, 2007, the entireties of which are incorporated herein by reference.

1. FIELD OF THE INVENTION

This invention relates to methods of synthesizing imidazole-based compounds.

2. BACKGROUND

The compound 1-(4-((1R,2S,3R)-1,2,3,4-tetrahydroxybutyl)-1H-imidazol-2-yl)ethanone (THI) is a minor constituent of Carmel Color III, and reportedly lowers circulating lymphocyte counts in rats. Methods of preparing THI have been reported. See, e.g., Kröplien, U. and Rosdorfer, J., *J. Org. Chem.* 50:1131-1133 (1985); U.S. Pat. No. 4,567,194 to Kröplien et al.; Cliff, M. D. and Pyne, S. G., *Tet. Lett.* 36(33): 5969-5972 (1995); Cliff, M. D. and Pyne, S. G., *J. Org. Chem.* 62:1023-1032 (1997). A particular method reportedly provides THI in an overall yield of 46%. See Halweg, K. M. and Büchi, G., *J. Org. Chem.* 50:1134-1136, 1135 (1985).

It was recently reported that certain imidazole-based compounds are potent inhibitors of immune response, and may be useful in the treatment of diseases such as rheumatoid arthritis and type I diabetes. See U.S. patent application Ser. No. 11/698,253 to Augeri et al., filed Jan. 25, 2007. In order to facilitate their testing and use, additional methods of their synthesis are desired.

3. SUMMARY OF THE INVENTION

This invention encompasses methods of preparing compounds of formula I:

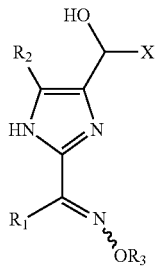

wherein: X is optionally substituted alkyl; $R_1$ is optionally substituted alkyl; $R_2$ is hydrogen, halogen, nitrile, or optionally substituted alkyl, aryl, alkylaryl, arylalkyl, heteroalkyl, heterocycle, alkylheterocycle, or heterocyclealkyl; and $R_3$ is hydrogen or optionally substituted alkyl, aryl, alkylaryl, arylalkyl, heteroalkyl, heterocycle, alkylheterocycle, or heterocyclealkyl.

This invention also encompasses methods of increasing the major to minor (major:minor) isomer ratios of mixtures of compounds of formula I.

The invention also encompasses methods of preparing 1-(4-((1R,2S,3R)-1,2,3,4-tetrahydroxybutyl)-1H-imidazol-2-yl)ethanone.

4. BRIEF DESCRIPTION OF THE FIGURE

Aspects of this invention can be understood with reference to FIG. 1, which shows a $^1$H NMR spectrum of a mixture of (E)-1-(4-((1R,2S,3R)-1,2,3,4-tetrahydroxybutyl)-1H-imidazol-2-yl)-ethanone oxime and (Z)-1-(4-((1R,2S,3R)-1,2,3,4-tetrahydroxybutyl)-1H-imidazol-2-yl)-ethanone oxime.

5. DETAILED DESCRIPTION

This invention is based, in part, on the discovery of novel methods of preparing compounds of formula I. Particular methods are well suited for the compounds' large-scale (e.g., kilogram scale) manufacture.

This invention is also based on the discovery of novel methods of making 1-(4-((1R,2S,3R)-1,2,3,4-tetrahydroxybutyl)-1H-imidazol-2-yl)ethanone. Particular methods afford the compound in high yield.

5.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$. The term "lower alkoxy" refers to —O-(lower alkyl).

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the term "E:Z isomer ratio," when referring to a mixture of an E isomer of a compound and its corresponding Z isomer, means the ratio of those isomers. Such ratios can be determined by various methods known in the art, including chromatographic (e.g., HPLC) and spectroscopic (e.g., NMR, Raman, and infrared absorption) methods.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the term "major:minor isomer ratio," when referring to a mixture of a two isomers of a compound—the major isomer (i.e., the isomer present in greater than 50 weight percent) and its corresponding minor isomer (i.e., the isomer present in less than 50 weight percent)—means the ratio of those isomers. Such ratios can be determined by various methods known in the art, including chromatographic (e.g., HPLC) and spectroscopic (e.g., NMR, Raman, and infrared absorption) methods. When used to refer to a compound containing an oxime moiety, the term "major:minor isomer ratio" refers to the oxime geometry. Thus, if a compound comprising an oxime moiety has additional stereocenters, the term refers to the ratio of diastereomers comprising the oxime in one configuration to the diastereomers comprising the oxime in the other.

Unless otherwise indicated, the term "stereomerically enriched composition of" a compound refers to a mixture of the named compound and its stereoisomer(s) that contains more of the named compound than its stereoisomer(s). For example, a stereoisomerically enriched composition of (S)-butan-2-ol encompasses mixtures of (S)-butan-2-ol and (R)-butan-2-ol in ratios of, e.g., about 60/40, 70/30, 80/20, 90/10, 95/5, and 98/2.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A stereomerically pure composition of a compound that has multiple stereocenters, but which is drawn or named in such a way that the stereochemistries of less than all of its stereocenters are defined, is substantially free of the isomers of the compound that have different stereochemistries at the stereocenters for which stereochemistry is defined. For example, "stereomerically pure ((1R)-1,2-dichloropropyl)benzene" refers to ((1R)-1,2-dichloropropyl)benzene that is substantially free of ((1S)-1,2-dichloropropyl)benzene.

A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl- or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

Unless otherwise indicated, the phrase "greater than X," where X is a number, has the same meaning as "X or greater than X." Similarly, the phrase "greater than about X," where X is a number, has the same meaning as "about X or greater than about X."

Unless otherwise indicated, the phrase "less than X," where X is a number, has the same meaning as "X or less than X." Similarly, the phrase "less than about X," where X is a number, has the same meaning as "about X or less than about X."

Unless otherwise indicated, the term "include" has the same meaning as "include" and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. Methods of Synthesis

This invention encompasses a method of preparing a compound of formula I:

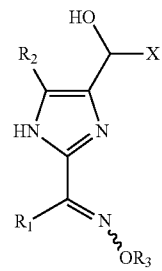

wherein: X is optionally substituted alkyl; R$_1$ is optionally substituted alkyl; R$_2$ is hydrogen, halogen, nitrile, or optionally substituted alkyl, aryl, alkylaryl, arylalkyl, heteroalkyl, heterocycle, alkylheterocycle, or heterocyclealkyl; and R$_3$ is hydrogen or optionally substituted alkyl, aryl, alkylaryl, arylalkyl, heteroalkyl, heterocycle, alkylheterocycle, or heterocyclealkyl; which comprises:

contacting a compound of formula II:

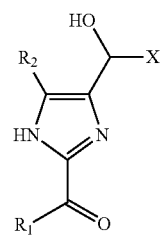

with a compound of formula III:

under conditions sufficient for the formation of a mixture of E and Z isomers of a compound of formula I; and contacting the mixture of E and Z isomers with a strong acid.

Another embodiment encompasses a method of increasing the major:minor isomer ratio in a mixture of compounds of formula I:

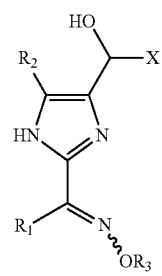

which comprises:

contacting a solution comprising a first mixture of compounds of formula I with a strong acid under conditions sufficient to provide a second mixture of compounds of formula I, wherein:

the major:minor isomer ratio of the first mixture is less than the major:minor isomer ratio of the second mixture; X is optionally substituted alkyl; $R_1$ is optionally substituted alkyl; $R_2$ is hydrogen, halogen, nitrile, or optionally substituted alkyl, aryl, alkylaryl, arylalkyl, heteroalkyl, heterocycle, alkylheterocycle, or heterocyclealkyl; and $R_3$ is hydrogen or optionally substituted alkyl, aryl, alkylaryl, arylalkyl, heteroalkyl, heterocycle, alkylheterocycle, or heterocyclealkyl.

In the various methods and embodiments disclosed herein, compounds (e.g., compounds of formulae I, II and/or III) may exist or be obtained as solvates and/or salts.

In a particular embodiment, the solution comprises an alcohol (e.g., methanol, ethanol, propanol or isopropanol).

In another, the solution is heated to a temperature of greater than about 30° C. (e.g., greater than about 40, 50 or 60° C.).

In another, the major:minor isomer ratio increases from less than about 5:1 to greater than about 8:1. In another, the major:minor isomer ratio increases from less than about 4:1 to greater than about 10:1. In another, the major:minor isomer ratio increases from about 3:1 to greater than about 13:1.

In another, the pH of the solution comprising the second mixture is increased. In particular methods, the pH is increased to greater than about 6.0 (e.g., greater than about 7.0 or 8.0).

With reference to the various methods disclosed herein, as appropriate, particular embodiments are such that X is alkyl optionally substituted with one or more hydroxyl, acetate or halogen moieties.

In others, $R_2$ is hydrogen.
In others, $R_3$ is hydrogen.
In others, the compound of formula I is of formula I(a):

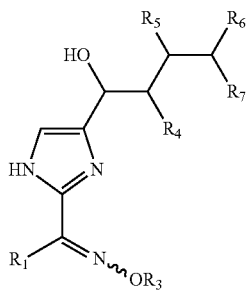

I(a)

wherein: $R_4$ is $OR_{4A}$, $OC(O)R_{4A}$, $N(R_{4B})_2$, $NHC(O)R_{4B}$, hydrogen, or halogen; $R_5$ is °$R_{5A}$, $OC(O)R_{5A}$, $N(R_{5B})_2$, $NHC(O)R_{5B}$, hydrogen, or halogen; $R_6$ is $OR_{6A}$, $OC(O)R_{6A}$, $N(R_{6B})_2$, $NHC(O)R_{6B}$, hydrogen, or halogen; $R_7$ is alkyl, $CH_2OR_{7A}$, $CH_2OC(O)R_{7A}$, $CH_2N(R_{7B})_2$, $CH_2NHC(O)R_{7B}$, hydrogen, or halogen; and each of $R_{4A}$, $R_{5A}$, $R_{6A}$, $R_{7A}$, $R_{4B}$, $R_{5B}$, $R_{6B}$, and $R_{7B}$ is independently hydrogen or optionally substituted alkyl, aryl, alkylaryl, arylalkyl, heteroalkyl, heterocycle, alkylheterocycle, or heterocyclealkyl.

In others, the compound of formula I(a) is a stereomerically pure compound of formula I(b):

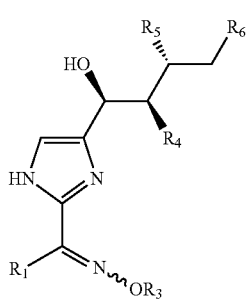

I(b)

Referring to structures I(a) and (b), particular embodiments of the invention are such that one or more of $R_4$, $R_5$, and $R_6$ is hydroxy or halogen. In others, all of $R_4$, $R_5$, and $R_6$ are hydroxyl or acetate.

Examples of strong acids include hydroiodic, hydrobromic, hydrochloric, sulfuric, nitric, phosphoric, alkanesulfonic, and arenesulfonic acid.

A specific embodiment of the invention is represented below, in Scheme 1:

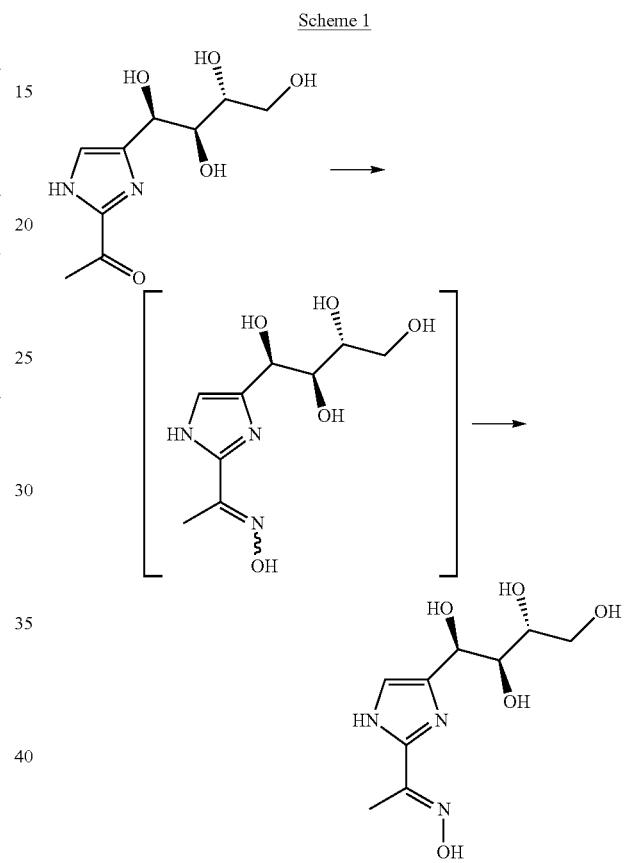

Scheme 1

In this method, the E:Z isomer ratio in a mixture of (E)-1-(4-((1R,2S,3R)-1,2,3,4-tetrahydroxybutyl)-1H-imidazol-2-yl)-ethanone oxime and (Z)-1-(4-((1R,2S,3R)-1,2,3,4-tetrahydroxybutyl)-1H-imidazol-2-yl)-ethanone oxime is increased.

The method comprises contacting a solution comprising a first mixture of (E)-1-(4-((1R,2S,3R)-1,2,3,4-tetrahydroxybutyl)-1H-imidazol-2-yl)-ethanone oxime and (Z)-1-(4-((1R,2S,3R)-1,2,3,4-tetrahydroxybutyl)-1H-imidazol-2-yl)-ethanone oxime with a strong acid under conditions sufficient to provide a second mixture of (E)-1-(4-((1R,2S,3R)-1,2,3,4-tetrahydroxybutyl)-1H-imidazol-2-yl)-ethanone oxime and (Z)-1-(4-((1R,2S,3R)-1,2,3,4-tetrahydroxybutyl)-1H-imidazol-2-yl)-ethanone oxime; wherein the E:Z isomer ratio of the first mixture is less than the E:Z isomer ratio of the second mixture.

In a particular embodiment, the first mixture is prepared by contacting 1-(4-((1R,2S,3R)-1,2,3,4-tetrahydroxybutyl)-1H-imidazol-2-yl)ethanone with hydroxylamine under conditions sufficient for the formation of 1-(4-((1R,2S,3R)-1,2,3,4-tetrahydroxybutyl)-1H-imidazol-2-yl)-ethanone oxime. The 1-(4-((1R,2S,3R)-1,2,3,4-tetrahydroxybutyl)-1H-imidazol-2-yl)ethanone can be prepared by contacting 1-amino-1- deoxy-D-fructose with 2-ethoxyacrylonitrile under conditions sufficient for the formation of 1-(4-((1R,2S,3R)-1,2,3,4-tetrahydroxybutyl)-1H-imidazol-2-yl)ethanone, as shown below in Scheme 2:

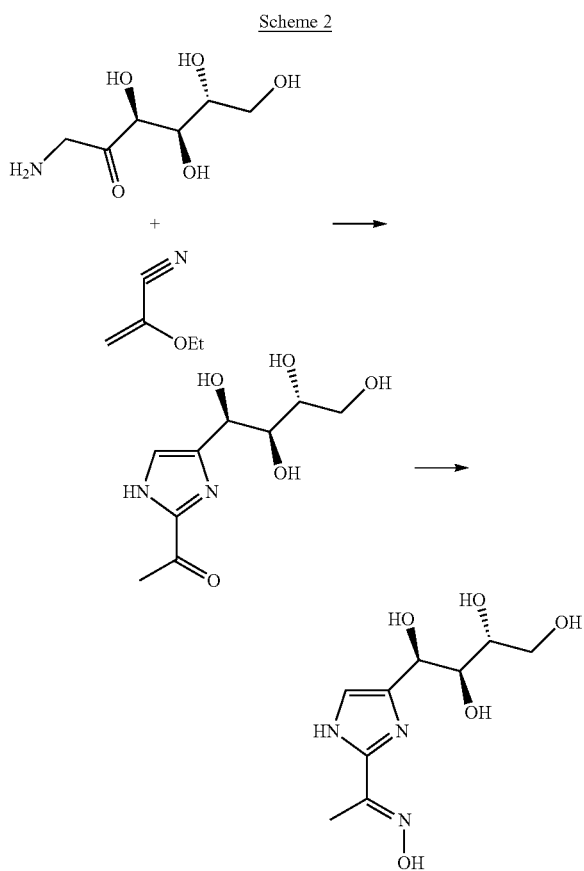

Advantageously, this invention provides novel methods of making 1-(4-((1R,2S,3R)-1,2,3,4-tetrahydroxybutyl)-1H-imidazol-2-yl)ethanone.

One embodiment encompasses a method of preparing 1-(4-((1R,2S,3R)-1,2,3,4-tetrahydroxybutyl)-1H-imidazol-2-yl)ethanone, which comprises: adding a first portion of sodium methoxide to a solution comprising 2-ethoxyacrylonitrile to provide a first mixture; contacting the first mixture with 1-amino-1-deoxy-D-fructose to provide a second mixture; adding a second portion of sodium methoxide to the second mixture to provide a third mixture; adding acetic acid to the third mixture to provide a fourth mixture; and mixing the fourth mixture for a time and at a temperature sufficient for the formation of 1-(4-((1R,2S,3R)-1,2,3,4-tetrahydroxybutyl)-1H-imidazol-2-yl)ethanone.

In a particular method, the second mixture is maintained at a temperature of greater than about 5° C. (e.g., greater than about 10, 15 or 20° C.).

In another, the first mixture is maintained at a temperature of greater than about 5° C. (e.g., greater than about 10, 15 or 20° C.).

In another, the first portion of sodium methoxide is added as a solution of greater than about 15 weight percent (e.g., greater than about 20 or 25 weight percent) sodium methoxide in methanol.

In another, the second portion of sodium methoxide is added as a solution of greater than about 15 weight percent (e.g., greater than about 20 or 25 weight percent) sodium methoxide in methanol.

In another, the 1-amino-1-deoxy-D-fructose is provided in a slurry further comprising its acetic acid salt.

In another, the third mixture is diluted with water before the acetic acid is added to it.

In another, the fourth mixture is heated to a temperature of greater than about 30° C. (e.g., greater than about 35, 40, 45, 50, 55, or 60° C.).

In another, the fourth mixture is heated for less than about 5 hours (e.g., less than about 4, 3, or 2 hours).

In another, the 1-(4-((1R,2S,3R)-1,2,3,4-tetrahydroxybutyl)-1H-imidazol-2-yl)ethanone is isolated with a yield of greater than about 50 percent (e.g., greater than about 55, 60, 65, 70, 75, or 80 percent).

6. EXAMPLES

Aspects of this invention can be understood from the following examples, which do not limit its scope.

6.1. Example 1

Preparation of Ethoxyacrylonitrile

To a 250 ml jacketed 3-neck round bottom flask with magnetic stir bar, rubber septum with temperature probe, plastic stopper, and pressure-equalized addition funnel with gas bubbler was charged with bromoacetaldehyde diethylacetal (35.33 g/179.28 mmol) and tin (II) chloride (167.1 mg/0.88 mmol/0.5 mol %). The suspension was cooled to 3° C. Then trimethylsilyl cyanide (17.69 g/178.31 mmol) was added over 11 minutes at a temperature below 15° C. The mixture was held at about 10° C. for 35 minutes and then at about 20° C. for at least 1.75 hours or until GC analysis showed consumption of bromoacetaldehyde diethylacetal.

The above light yellow solution was diluted with 85 ml MTBE. Diethylamine (19.61 g, 268.11 mmol/1.50 equiv.) was added over 6 minutes at a temperature below 35° C. The resulting thick slurry was diluted with additional 25 ml MTBE. The reaction mixture was stirred at about 25° C. for at least 1.75 hours or until reaction completion by GC analysis. The mixture was filtered and the collected solids were washed MTBE (2×30 ml). The combined filtrate was concentrated under vacuum (final vacuum: about 95 torr). The resulting crude ethoxyacrylonitrile (17.46 g) was polish-filtered and vacuum distilled to give a clear liquid (11.2 g, 67% yield). B.p.: 46-49° C./31 mm Hg. $^1$H NMR (CDCl$_3$) δ 4.85 (d, J=3.54 Hz, 1H), 4.75 (d, J=3.28 Hz, 1H), 3.73 (q, J=6.99 Hz, 2H), 1.24 (t, J=6.95 Hz, 3H). $^{13}$C NMR (CDCl$_3$) δ 136.58, 115.23, 101.11, 65.54, 14.40.

6.2. Example 2

Preparation of 1-(4-((1R,2S,3R)-1,2,3,4-tetrahydroxybutyl)-1H-imidazol-2-yl)ethanone To a 3-neck, 12-L round bottom flask equipped with a mechanical stirrer, a temperature controller was added ethoxyacrylonitrile (100.0 g, 1.03 mol) and methanol (HPLC grade, 1.0 L, 10×). To the above stirred solution was added sodium methoxide in methanol (25 wt %, 140.6 ml, 0.60 equiv) in over 15 minutes. The mixture was stirred at 20° C. for at least 3 hours or until $^1$H NMR showed at least 95% conversion of the ethoxyacrylonitrile to the corresponding imidate). The above solution was transferred to a slurry of fructosamine acetic acid salt (246.9 g, 1.0 equiv, prepared according to Hodge, J. E.; Fisher, B. E., *Methods in Carbohydrate Chemistry* 11:99-103 (1963)) in methanol (1.0 L, 10×) over 15 min and the mixture was stirred at 20° C. for 6 hours. Another portion of sodium methoxide in methanol (25 wt %, 117.3 ml, 0.50 equiv) was added to the mixture over 10 minutes and the mixture stirred at 20° C. for additional 16 hours.

The mixture was then diluted with water (2.0 L, 20×) and treated with acetic acid (118 ml, 2.0 equiv). After stirring at 60° C. for 1 h, the solution was concentrated (50° C., 200 mbar-70 mbar) to 1.2 L total volume. The slurry mixture was cooled to 0° C. and stirred for 1 h, then filtered and the solids were washed with water (100 ml, ×2). The solids were collected and dried under vacuum at 50° C. to afford 196.8 g crude product as a pale yellow solid, which was then treated with water (980 ml, 5×) and the resulting slurry was heated to boiling for 15 min, then re-cooled to 0° C. and stirred for an additional 1 h. The mixture was again filtered, and the solids were washed with water (100 ml, ×2) and dried to constant weight in a vacuum oven at 50° C. to provide 194.8 g (82%) of the title product (THI) as a pale yellow solid (KF=0.4%). $^1$H NMR (D$_2$O w/a drop of DCl in D$_2$O) 7.48 (d, J=2.0 Hz, 0.9H), 7.19 (d, J=2.0 Hz, 0.1H), 5.09 (s, 0.9H), 4.98 (s, 0.1H), 3.40-3.70 (m, 4H), 2.53 (d, J=2.4 Hz, 3H); $^{13}$C NMR (D$_2$O w/a drop of DCl in D$_2$O) 185.0, 139.4, 138.0, 119.5, 73.0, 70.9, 65.0, 63.2, 26.7; MH$^+$=231.2.

6.3. Example 3

Preparation of (E)-1-(4-((1R,2S,3R)-1,2,3,4-Tetrahydroxybutyl)-1H-imidazol-2-yl)-ethanone Oxime Dihydrate To a 3-neck, 3-L round bottom flask equipped with a mechanical stirrer, a temperature controller and a condenser were charged with 1-(4-((1R,2S,3R)-1,2,3,4-tetrahydroxybutyl)-1H-imidazol-2-yl)ethanone (100.0 g, 434.4 mmol), hydroxylamine hydrochloric acid salt (45.2 g, 1.5 equiv), sodium acetate (53.4 g, 1.5 equiv) and methanol (HPLC grade, 1.0 L, 10×). The above solution was heated at 65° C. with stirring for 2 h.

To the mixture was then added a solution of HCl in isopropanol (freshly prepared by slow addition of 92.7 ml acetyl chloride to 200 ml isopropanol at 0° C., 3.0 equiv) over 15 min and resulting mixture stirred at 65° C. for 3 h. The mixture was diluted with MeOH (1.0 L, 10×) and cooled to room temperature and the precipitated sodium chloride was removed by filtration. The solids were washed with MeOH (100 ml, 1×) and the solution was concentrated at 40° C. under vacuum until solids started to form (about 200 ml). Water (1.0 L, 10×) was then added and the residual organic solvents were removed at 40° C. under vacuum. A polish filtration was performed to afford a clear yellow solution. To this solution was slowly added 50% NaOH aqueous solution at room temperature so that the temperature of the mixture did not exceed 40° C., until the pH reached 7.2 (7.0-7.5). The resulting solution was then heated to 65° C. to form a homogeneous solution, and concentrated under vacuum at 65° C. (60-70° C.) until the solution reached about 500 ml (5×) overall volume. The mixture was then cooled to room temperature slowly, further cooled to 0° C., and stirred at 0° C. for 1 h. The solids were collected by filtration and washed with water (0° C., 100 ml, 1× ×2) to afford a white crystalline solid.

To the above wet solid was added water (400 ml) and the resulting mixture was heated to 70-80° C. until all dissolved. The solution was cooled to room temperature and then stirred at 0° C. for 1 h. The solids were collected by filtration and washed with water (0° C., 100 ml, 1× ×2) and then dried under vacuum at 30° C. overnight to afford 99.4 g of the title compound. NMR analysis showed that the material contained about 3% of the Z isomer.

6.4. Example 4

Preparation of Anhydrous (E)-1-(4-((1R,2S,3R)-1,2,3,4-Tetrahydroxybutyl)-1H-imidazol-2-yl)-ethanone Oxime The solid from Example 3 was slurried with EtOH (800 ml, 8×) and heated at 75° C. for 1 h. The resulting mixture was cooled to 0° C. and stirred at 0° C. for 1 h. The white solid was collected by filtration and washed with EtOH (0° C., 100 ml, 1×, ×2) and dried at 50° C. under vacuum to constant weight to give the title compound. NMR analysis showed about 2% of the Z isomer. $^1$H NMR (D$_2$O) 7.05 (s, 1H), 4.83 (d, J=3.6 Hz, 1H), 3.60-3.80 (m, 3H), 3.50 (dd, J=11.6, 6.8 Hz, 1H), 2.11 (d, J=4.0 Hz, 3H); $^1$H NMR (D$_2$O w/a drop of DCl in D$_2$O) 7.30 (s, 1H), 5.04 (s, 1H), 3.45-3.75 (m, 4H), 2.13 (s, 3H); $^{13}$C NMR (D$_2$O w/a drop of DCl in D$_2$O) 143.8, 140.9, 135.0, 116.9, 72.5, 70.6, 64.4, 62.7, 10.5; MH$^+$=246.1.

6.5. Example 5

Determination of E:Z Isomers Ratios

The relative amounts of E and Z isomers of compounds of Formula I can be determined by a variety of techniques known in the art. For example, the relative amounts of (E)-1-(4-((1R,2S,3R)-1,2,3,4-tetrahydroxybutyl)-1H-imidazol-2-yl)-ethanone oxime and (Z)-1-(4-((1R,2S,3R)-1,2,3,4-tetrahydroxybutyl)-1H-imidazol-2-yl)-ethanone oxime in a mixture of the two can be readily determined by NMR, as shown in FIG. 1.

All cited publications, patents, and patent applications are herein incorporated by reference in their entireties.

What is claimed is:

1. A composition compising an alcohol and (E)-1-(4-((1R,2S,3R)-1,2,3,4-tetrahydroxybutyl)-1H-imidazol-2-yl)-ethanone oxime and (Z)-1-(4-((1R,2S,3R)-1,2,3,4-tetrahydroxybutyl)-1H-imidazol-2-yl)-ethanone oxime in an E:Z isomer ratio that is greater than 8:1.

2. The composition of claim 1, wherein the E:Z isomer ratio is greater than 10:1.

3. The composition of claim 2, wherein the E:Z isomer ratio is greater than 13:1.

4. The composition of claim 1, wherein the alcohol is methanol, ethanol, propanol, or isopropanol.

5. The composition of claim 4, wherein the alcohol is methanol.

6. The composition of claim 1, which is acidic.

7. The composition of claim 6, which is acidic due to the addition of an acid which is hydroiodic, hydrobromic, hydrochloric, sulfuric, nitric, phosphoric, alkanesulfonic, or arenesulfonic acid.

8. The composition of claim 7, wherein the acid is hydrochloric acid.

\* \* \* \* \*